United States Patent
Avidov et al.

(10) Patent No.: US 8,946,513 B2
(45) Date of Patent: *Feb. 3, 2015

(54) POLYPLOID CASTOR PLANTS, COMPOSITIONS DERIVED THEREFROM AND USES OF SAME

(71) Applicant: Kaiima Bio Agritech Ltd., Kfar-Tavor (IL)

(72) Inventors: Amit Avidov, Kiryat-Tivon (IL); Alon Lerner, Moshav Sharona (IL)

(73) Assignee: Kaiima Bio Agritech Ltd., Kfar-Tavor (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/892,366

(22) Filed: May 13, 2013

(65) Prior Publication Data

US 2013/0254913 A1   Sep. 26, 2013

Related U.S. Application Data

(63) Continuation of application No. 12/741,599, filed as application No. PCT/IL2008/001470 on Nov. 6, 2008.

(60) Provisional application No. 60/996,214, filed on Nov. 6, 2007.

(51) Int. Cl.
 *A01H 1/00* (2006.01)
 *A01H 5/00* (2006.01)
 *A01H 5/10* (2006.01)
 *H01H 5/10* (2006.01)

(52) U.S. Cl.
 CPC ... *A01H 5/00* (2013.01); *H01H 5/10* (2013.01)
 USPC ............ 800/295; 435/410; 800/260; 800/298

(58) Field of Classification Search
 None
 See application file for complete search history.

(56) References Cited

U.S. PATENT DOCUMENTS

| | | |
|---|---|---|
| 6,441,278 B1 | 8/2002 | DeBonte et al. |
| 2014/0121392 A1 | 5/2014 | Avidov et al. |
| 2014/0223594 A1 | 8/2014 | Avidov et al. |

FOREIGN PATENT DOCUMENTS

| | | |
|---|---|---|
| JP | 63-084429 | 4/1988 |
| WO | WO 2009/060451 | 5/2009 |
| WO | WO 2009/060455 | 5/2009 |

OTHER PUBLICATIONS

Sidorov et al 1941, Armyanskiy Khimicheskiy Zhurnal 31(3): 264-265 (in Russian with attached English translation).*
Preliminary Conclusion of Qualification Examination on Patentability Dated Sep. 9, 2013 From the State Intellectual Property Service of Ukraine, Ukrainian Institute of Industrial Property Re. Application No. 201007076 and Its Summary in English.
Applicant-Initiated Interview Summary Dated Nov. 20, 2013 From the US Patent and Trademark Office Re. U.S. Appl. No. 12/741,376.
Applicant-Initiated Interview Summary Dated Nov. 21, 2013 From the US Patent and Trademark Office Re. U.S. Appl. No. 12/741,599.
Communication Pursuant to Article 94(3) EPC Dated Dec. 2, 2013 From the European Patent Office Re. Application No. 13153253.3.
Notification of the Need to Submit Additional Materials Dated Nov. 13, 2013 From the Eurasian Patent Organization, The Eurasian Patent Office Re. Application No. 201000737 and Its Summary in English.
Translation of Office Action Dated Jun. 8, 2013 From the State Intellectual Property Office of the People's Republic of China Re. Application No. 200880124139.X.
Translation of Office Action Dated Jun. 9, 2013 From the State Intellectual Property Office of the People's Republic of China Re. Application No. 200880124137.0.
European Search Report and the European Search Opinion Dated Jul. 30, 2013 From the European Patent Office Re. Application No. 13151699.9.
Official Action Dated Sep. 16, 2013 From the US Patent and Trademark Office Re. U.S. Appl. No. 12/741,376.
Communication Pursuant to Rules 70(2) and 70a(2) EPC and References to Rule 39(1) EPC Dated Sep. 2, 2013 From the European Patent Office Re. Application No. 13151699.9.
Notice of Allowance Dated Jan. 3, 2014 From the US Patent and Trademark Office Re. U.S. Appl. No. 12/741,376.
Summons to Attend Oral Proceedings Pursuant to Rule 115(1) EPC Dated May 31, 2013 From the European Patent Office Re. Application No. 08846788.1.
Notification of the Need for Additional Materials Dated Apr. 18, 2013 From the Eurasian Patent Organization, The Eurasian Patent Office Re. Application No. 201000737 and Its Summary in English.
Patent Examination Report Dated May 20, 2013 From the Australian Government, IP Australia Re. Application No. 2008326013.
Notification About Necessity to Submit Additional Materials Dated Aug. 19, 2013 From the Eurasian Patent Organization, The Eurasian Patent Office Re. Application No. 201000736 and Its Summary in English.
Office Action Dated Aug. 18, 2013 From the Israel Patent Office Re. Application No. 205557 and Its Translation Into English.
Wikipedia "Colchicine", Wikipedia, the Free Encyclopedia, 8 P., Last Modified Sep. 16, 2013.
Communication Pursuant to Article 94(3) EPC Dated Dec. 6, 2012 From the European Patent Office Re. Application No. 08848502.4.
Communication Pursuant to Article 94(3) EPC Dated Feb. 10, 2012 From the European Patent Office Re. Application No. 08846788.1.
Communication Pursuant to Article 94(3) EPC Dated Jan. 12, 2011 From the European Patent Office Re. Application No. 08846788.1.
Communication Pursuant to Article 94(3) EPC Dated Jan. 24, 2011 From the European Patent Office Re. Application No. 08848502.4.
Communication Pursuant to Article 94(3) EPC Dated Dec. 29, 2011 From the European Patent Office Re. Application No. 08848502.4.

(Continued)

*Primary Examiner* — David H Kruse

(57) ABSTRACT

A polyploid castor plant being at least as fertile as a diploid castor plant isogenic to the polyploid castor plant when grown under similar conditions.

9 Claims, 8 Drawing Sheets

(6 of 8 Drawing Sheet(s) Filed in Color)

(56) References Cited

OTHER PUBLICATIONS

European Search Report and the European Search Opinion Dated Feb. 28, 2013 From the European Patent Office Re. Application No. 13153253.3.
International Preliminary Report on Patentability Dated May 20, 2010 From the International Bureau of WIPO Re.: Application No. PCT/IL2008/001468.
International Preliminary Report on Patentability Dated May 20, 2010 From the International Bureau of WIPO Re.: Application No. PCT/IL2008/001470.
International Search Report Dated Mar. 4, 2009 From the International Searching Authority Re.: Application No. PCT/IL2008/001470.
International Search Report Dated Feb. 18, 2009 From the International Searching Authority Re.: Application No. PCT/IL2008/001468.
Notification About Necessity to Submit Additional Materials Dated Feb. 8, 2013 From the Eurasian Patent Organization, The Eurasian Patent Office Re. Application No. 201000736 and Its Summary in English.
Notification About Necessity to Submit Additional Materials Dated Jun. 12, 2012 From the Eurasian Patent Organization, The Eurasian Patent Office Re. Application No. 201000736 and Its Translation Into English.
Office Action Dated Mar. 5, 2013 From the Israel Patent Office Re. Application No. 205558 and Its Translation Into English.
Office Action Dated Jan. 26, 2012 From the Israel Patent Office Re. Application No. 205557 and Its Translation Into English.
Office Action Dated Jan. 26, 2012 From the Israel Patent Office Re. Application No. 205558 and Its Translation Into English.
Official Action Dated Jul. 13, 2012 From the US Patent and Trademark Office Re. U.S. Appl. No. 12/741,599.
Official Action Dated May 21, 2012 From the US Patent and Trademark Office Re. U.S. Appl. No. 12/741,376.
Official Action Dated Jan. 22, 2013 From the US Patent and Trademark Office Re. U.S. Appl. No. 12/741,599.
Official Action Dated Nov. 29, 2012 From the US Patent and Trademark Office Re. U.S. Appl. No. 12/741,376.
Preliminary Conclusion of Qualification Examination Dated Feb. 5, 2013 From the State Intellectual Property Service of Ukraine, Ukrainian Institute of Industrial Property Re. Application No. 201007076 and Its Summary in English.
Response Dated Aug. 1, 2011 to Communication Pursuant to Article 94(3) EPC of Jan. 24, 2011 From the European Patent Office Re. Application No. 08848502.4.
Response Dated Jul. 11, 2011 to Communication Pursuant to Article 94(3) EPC of Jan. 12, 2011 From the European Patent Office Re. Application No 08846788.1.
Response Dated Jul. 18, 2011 to Communication Pursuant to Article 94(3) EPC of Jan. 24, 2011 From the European Patent Office Re. Application No. 08848502.4.
Restriction Official Action Dated Apr. 13, 2012 From the US Patent and Trademark Office Re. U.S. Appl. No. 12/741,599.
Restriction Official Action Dated Feb. 27, 2012 From the US Patent and Trademark Office Re. U.S. Appl. No. 12/741,376.
Translation of Office Action Dated Sep. 19, 2012 From the State Intellectual Property Office of the People's Republic of China Re. Application No. 200880124139.X.
Translation of Office Action Dated Aug. 30, 2012 From the State Intellectual Property Office of the People's Republic of China Re. Application No. 200880124137.0.
Translation of Search Report Dated Sep. 19, 2012 From the State Intellectual Property Office of the People's Republic of China Re. Application No. 200880124139.X.
Translation of Search Report Dated Aug. 30, 2012 From the State Intellectual Property Office of the People's Republic of China Re. Application No. 200880124137.0.
Written Opinion Dated Mar. 4, 2009 From the International Searching Authority Re.: Application No. PCT/IL2008/001470.
Written Opinion Dated Feb. 18, 2009 From the International Searching Authority Re.: Application No. PCT/IL2008/001468.
Appelqvist "Lipids in Cruciferae. III. Fatty Acid Composition of Diploid and Tetraploid Seeds of *Brassica campestris* and *Sinapis alba* Grown Under Two Climatic Extremes", Physiologia Plantarum, 21(3): 615-625, Mar. 1968. Abstract.
Ben-Ner "Multiplication of Genome. A Way to Improve Productivity of Energy Crops", BF-Agritech Ltd., 4 P., Nov. 2006.
Bhattacharya et al. "Effect of Magnetic Field on the Living Cells and Chromosomes", 6th Lowrad Conference, XP002515948, Budapest, Hungary, Oct. 17-20, 2007. Abstract.
BioFuel "BioFuel MS", BioFuel International Ltd., 2 P., Oct. 2007.
BioFuel "Sustainability—Multiplied", BioFuel international Ltd., 14 P., Oct. 2007.
BioFuel "XL Seed Change in Energy", BioFuel International Ltd., 1 P., Oct. 2007.
Chen et al. "Studies on Polyploid Induction of Tomato With Colchicine", Shandong Agricultural Sciences, 3: 22-24, 2007. Abstract in English.
Chen et al. "Studies on Polyploid Induction of Tomato With Colchicine", Shandong Agricultural Sciences, 3: 22-24, 2007. English Translation.
Davies et al. "Floral Nectar Secretion and Ploidy in *Brassica rapa* and *B. napus* (Brassicaceae). II. Quantified Variability of Nectary Structure and Function in Rapid-Cycling Lines", Annals of Botany, 77: 223-234, 1996.
De et al. "Stability of Rape Genome", Journal of West Henan Agricultural College, 3: 49-53, 1990. Chinese Only!
Jakob "A Trisomic Male Castor Bean Plant", Journal of Heredity, 54(6): 292-296, 1963.
Kudo et al. "Flow Cytometric Evidence for Endopolyploidy in Seedlings of Some *Brassica* Species", Theoretical and Applied Genetics, XP009111736, 102(1): 104-110, Jan. 2001.
Mederos Molina et al. "Micropropagation of *Ricinus communis*", Journal of Plant Physiology, 147: 270-272, 1995.
Moshkin "Genetics and Breeding of Castor. Cytology and Genetics of Qualitiative Characteristics", Castor, Chap.5: 93-133, 1986.
Osborn et al. "Understanding Mechanisms of Novel Gene Expression in Polyploids", Trends in Genetics, XP004411460, 19(3): 141-147, Mar. 1, 2003.
Sidorov "Production of Tetraploids in Castor Oil Plant *Ricinus communis* by the Action of Colchicine", Armyanskiy Khimicheskiy Zhurnal, 31(3): 264-265, 1941 and Its Translation Into English.
Tai et al. "Incomplete Bivalent Pairing in Dihaploids of *Brassica napus* L", Genome, XP001538976, 30(3): 450-457, 1988.
Timko et al. "Euploidy in *Ricinus*. Euploidy Effects on Photosynthetic Activity and Content of Chlorophyll-Proteins", Plant Physiology, XP002515947, 67: 1084-1089, 1981.
Timko et al. "Euploidy in *Ricinus*. I. Euploidy and Gene Dosage Effects on Cellular Proteins", Biochemical Genetics, 18(1/2): 171-183, 1980.
Timko et al. "Freeze-Fracture Architecture and Polypeptide Composition of Thylakoid Membranes From Euplid *Ricinus* Cells", Journal of Cell Science, XP002515946, 52: 167-181, 1981. Abstract, 'Materials and Method'.
Zhou et al. "Efficient Production of Doubled Haploid Plants by Immediate Colchicine Treatment of Isolated Microspores in Winter *Brassica napus*", Plant Growth Regulation, XP009111834, 37(2): 185-192, Jun. 2002.
Zhou et al. "Increasing Embryogenesis and Doubling Efficiency by Immediate Colchicine Treatment of Isolated Microspores in Spring *Brassica napus*", Euphytica, XP009111664, 1280): 27-34, 2002.
Zhou et al. "Studies on Efficient Production of Doubled Haploid Plants by Colchicine Treatments in Microspore Culture of *Brassica napus*", Agriculture Sciences in China, 35(4): 410-414, 2002. Chinese Only!
Communication Pursuant to Article 94(3) EPC Dated Dec. 10, 2013 From the European Patent Office Re. Application No. 08848502.4.
Communication Under Rule 71(3) EPC Dated Dec. 12, 2013 From the European Patent Office Re. Application No. 08846788.1.
Communication Pursuant to Rules 70(2) and 70a(2) EPC and Reference to Rule 39(1) EPC Dated May 14, 2013 From the European Patent Office Re. Application No. 13153253.3.

(56) References Cited

OTHER PUBLICATIONS

Office Action Dated Aug. 4, 2014 From the State Intellectual Property Office of the People's Republic of China Re. Application No. 200880124139.X and Its Translation Into English.
Communication Under Rule 71(3) EPC Dated Apr. 24, 2014 From the European Patent Office Re. Application No. 08846788.1.
Requisition by the Examiner Dated Jul. 10, 2014 From the Canadian Intellectual Property Office Re. Application No. 2,704,819.
Office Action Dated Feb. 8, 2014 From the State Intellectual Property Office of the People's Republic of China Re. Application No. 200880124139.X and Its Translation Into English.
Official Action Dated Feb. 26, 2014 From the US Patent and Trademark Office Re. U.S. Appl. No. 14/149,845.
Official Action Dated Feb. 27, 2014 From the US Patent and Trademark Office Re. U.S. Appl. No. 12/741,599.
Office Action Dated Mar. 18, 2014 From the Israel Patent Office Re. Application No. 205558 and Its Translation Into English.
Communication Pursuant to Article 94(3) EPC Dated Mar. 28, 2014 From the European Patent Office Re. Application No. 13151699.9.
Preliminary Conclusion of Qualification Examination Dated Mar. 11, 2014 From the State Intellectual Property Service of Ukraine, Ukrainian Institute of Industrial Property Re. Application No. 201007076 and Its Summary in English.
Office Action Dated Aug. 4, 2014 From the State Intellectual Property Office of the People's Republic of China Re. Application No. 200880124137.0 and Its Translation Into English.
Summons to Attend Oral Proceedings Pursuant to Rules 115(1) EPC Dated Jun. 20, 2014 From the European Patent Office Re. Application No. 08848502.4.
Office Action Dated Feb. 10, 2014 From the State Intellectual Property Office of the People's Republic of China Re. Application No. 200880124137.0 and Its Translation Into English.
Notification About Necessity to Submit Additional Materials Dated Apr. 25, 2014 From the Eurasian Patent Organization, The Eurasian Patent Office Re. Application No. 201000736 and Its Summary in English.
Notification of the Need to Submit Additional Materials Dated Aug. 28, 2014 From The Eurasian Patent Orgaization, The Eurasian Patent Office Re. Application No. 201000737 and Its Summary in English.

* cited by examiner

FIG. 5A-B

POLYPLOID CASTOR PLANTS, COMPOSITIONS DERIVED THEREFROM AND USES OF SAME

RELATED APPLICATIONS

This application is a continuation of U.S. patent application Ser. No. 12/741,599 filed on May 6, 2010, which is a National Phase of PCT Patent Application No. PCT/IL2008/001470 filed on Nov. 6, 2008, which claims the benefit of priority from U.S. Provisional Patent Application No. 60/996,214, filed Nov. 6, 2007.

The contents of all of the above documents are incorporated by reference as if fully set forth herein.

FIELD AND BACKGROUND OF THE INVENTION

The present invention, in some embodiments thereof, relates to polyploid castor plants and more particularly, but not exclusively, to compositions derived therefrom and uses of same.

Castor (*Ricinus communis* L.) is an important crop of the family Euphorbiaceae. It is a monotypic species of the genus *Ricinus* and has considerable economic value because of its oil-rich seeds, which yield castor oil, a strategically important oil with numerous industrial uses. Its origin is in the Southwestern Mediterranean and West Africa, but it is now common in many parts of the globe.

The castor bean contains up to 40-50% oil of unique composition. Chemically, castor is a triglyceride (ester) of fatty acids. Up to 90% of the fatty acid content of the oil is ricinoleic acid (12-hydroxyoleic acid), an 18-carbon acid having a double bond in the 9-10 position and a hydroxyl group on the 12th carbon. Castor oil ranges in color from colorless to yellowish or greenish. Additional characteristics include relatively high viscosity, non-drying, faint but characteristic odor slightly acrid taste and an aftertaste taste (what's an aftertaste taste?).

Many derivatives can be produced which have a similar chemical composition to petroleum based oils. Blown Castor oil is a derivative that has a higher viscosity and specific gravity compared to natural castor oil. These properties are induced by bubbling air through it at elevated temperatures. Its main use is as a plasticizer for inks, lacquers and adhesives. Hydrogenated castor oil (HCO) or castor wax is a hard, brittle wax that is insoluble. It is produced by adding hydrogen in the presence of a nickel catalyst. It is mainly used for coatings and greases where resistance to moisture, oils and other petrochemical products is required.

As a result, castor oil and products derived therefrom are used for numerous industrial products, including bio-based lubricants, fuel, paints and coatings, plastics, anti-fungal compounds, and cosmetics. The world market for castor oil is about 750 million dollars per year.

One problem in recent years has been the instability in the supply of castor oil. The major suppliers, India, China and Brazil, have experienced production problems in recent years.

Castor oil is a candidate feedstock for the emerging biodiesel industry, but it is currently too expensive to compete with petroleum based diesel. Increasing castor yields around the world can make castor-biodiesel more competitive in the future.

Autotetraploids have been produced using colchicine, in addition haploids have been reported, but in nature, castor is found mainly in the diploid form (Moshkin and Doryadinka, 1986).

SUMMARY OF THE INVENTION

According to an aspect of some embodiments of the present invention there is provided a polyploid castor plant being at least as fertile as a diploid castor plant isogenic to the polyploid castor plant when grown under similar conditions.

According to some embodiments of the invention, the fertility is determined by at least one of:
number of seeds per plant;
gamete fertility assay; and
acetocarmine pollen staining.

According to some embodiments of the invention, the plant exhibits genomic stability for at least 5 passages.

According to some embodiments of the invention, the plant has seed yield at least as similar to that of a the diploid castor plant.

According to some embodiments of the invention, the plant has a larger surface area of a leaf than that of the diploid castor plant.

According to some embodiments of the invention, the plant has larger stomata surface than that of the diploid castor plant.

According to some embodiments of the invention, the plant is a tetraploid.

According to some embodiments of the invention, the plant has oil yield at least as similar to that of the diploid castor plant.

According to some embodiments of the invention, the plant is capable of cross-breeding with a diploid plant.

According to some embodiments of the invention, the plant is an autopolyploid.

According to some embodiments of the invention, the plant is an inbred.

According to an aspect of some embodiments of the present invention there is provided a castor plant as deposited under the Budapest treaty in NCIMB Ltd. and having Accession No. NCIMB 41593 *Ricinus communis* B2-20-4N.

According to an aspect of some embodiments of the present invention there is provided a plant part of the castor plant.

According to an aspect of some embodiments of the present invention there is provided castor oil produced from the plant or plant part.

According to an aspect of some embodiments of the present invention there is provided a castor meal produced from the plant or plant part.

According to some embodiments of the invention the plant part is a seed.

According to an aspect of some embodiments of the present invention there is provided an isolated regenerable cell of the castor plant.

According to some embodiments of the invention the cell exhibits genomic stability for at least 5 passages in culture.

According to some embodiments of the invention the cell is from a mertistem, pollen, a leaf, a root, a root tip, an anther, a pistil, a flower, a seed or a stem.

According to an aspect of some embodiments of the present invention there is provided a tissue culture comprising the regenerable cells.

According to an aspect of some embodiments of the present invention there is provided a method of producing castor seeds, comprising self-breeding or cross-breeding the plant.

According to an aspect of some embodiments of the present invention there is provided a method of producing castor oil, the method comprising:

(a) harvesting seeds of the castor plant or plant part; and
(b) processing the seeds so as to produce the castor oil.

According to an aspect of some embodiments of the present invention there is provided a method of generating a polyploid castor seed, the method comprising contacting the castor seed with a G2/M cell cycle inhibitor under a magnetic field thereby generating the polyploid castor seed.

According to some embodiments of the invention the G2/M cell cycle inhibitor comprises a microtubule polymerization inhibitor.

According to some embodiments of the invention the microtubule polymerization inhibitor is selected from the group consisting of colchicine, nocodazole, oryzaline, trifluraline and vinblastine sulphate.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is picture of a polyploid castor plant generated according to the teachings of the present invention;

Figure 2A:
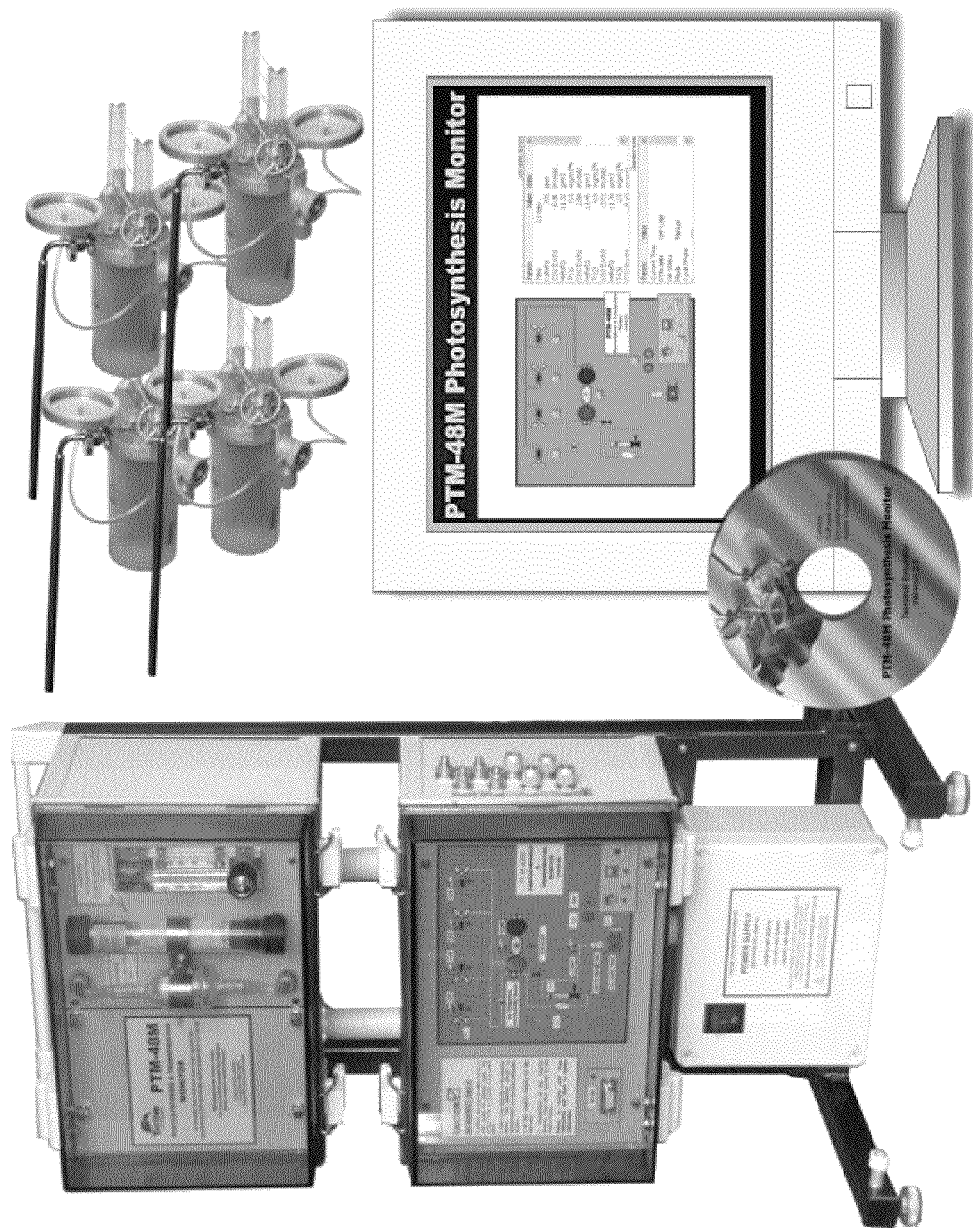
Figure 2B:

FIGS. 2A-B are images of a photosynthesis monitoring system used to evaluate photosynthesis efficiency in accordance with some embodiments of the present invention.

Figure 3A:
Figure 3B:
Figure 4:
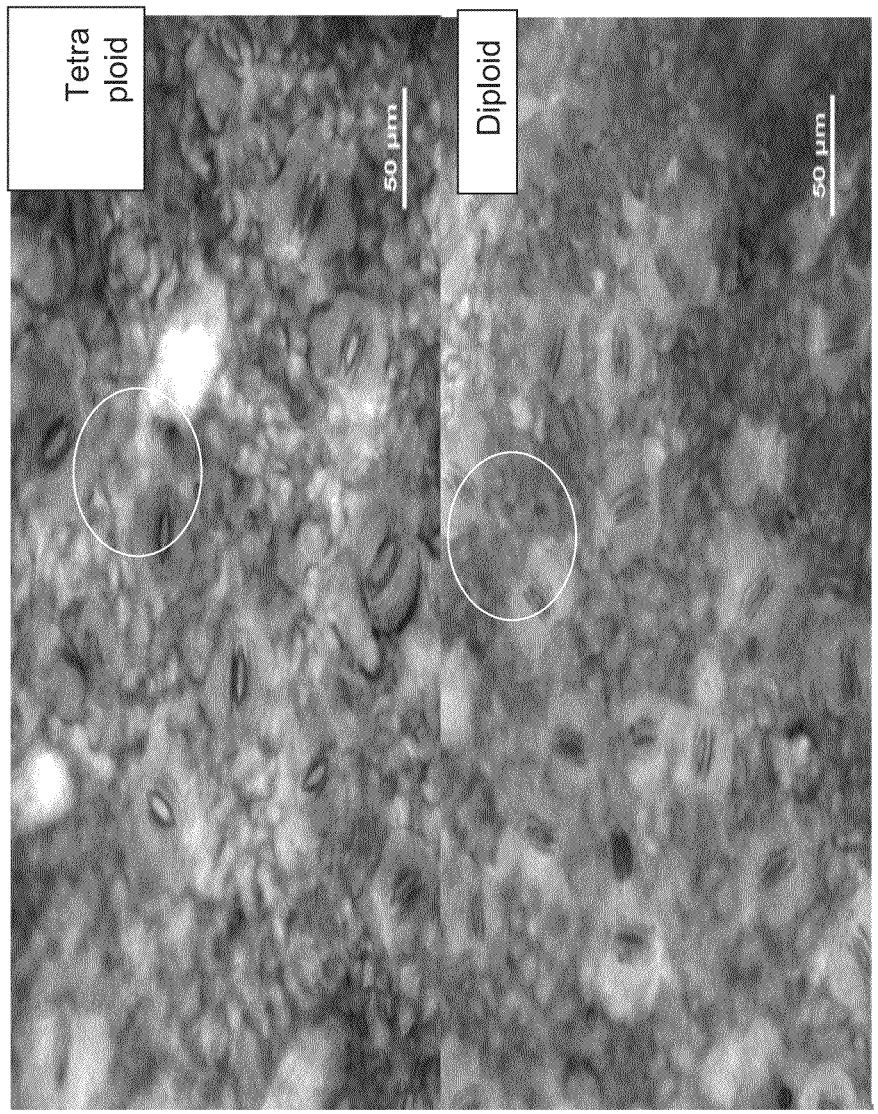

FIGS. 3A-B are pictures showing a diploid castor plant (3A) and a tetraploid castor plant (3B). The leaf chambers (LC) are given as a reference for the size of the leaves. Note that the leaves of the diploid plant were much smaller than the leaves of the tetraploids;

FIG. 4 is a photomicrograph image of stomata taken by a computerized microscope. Top: Tetraploid plant. Bottom Diploid plant (Example of stomata is circled with a white line).

Figure 5:
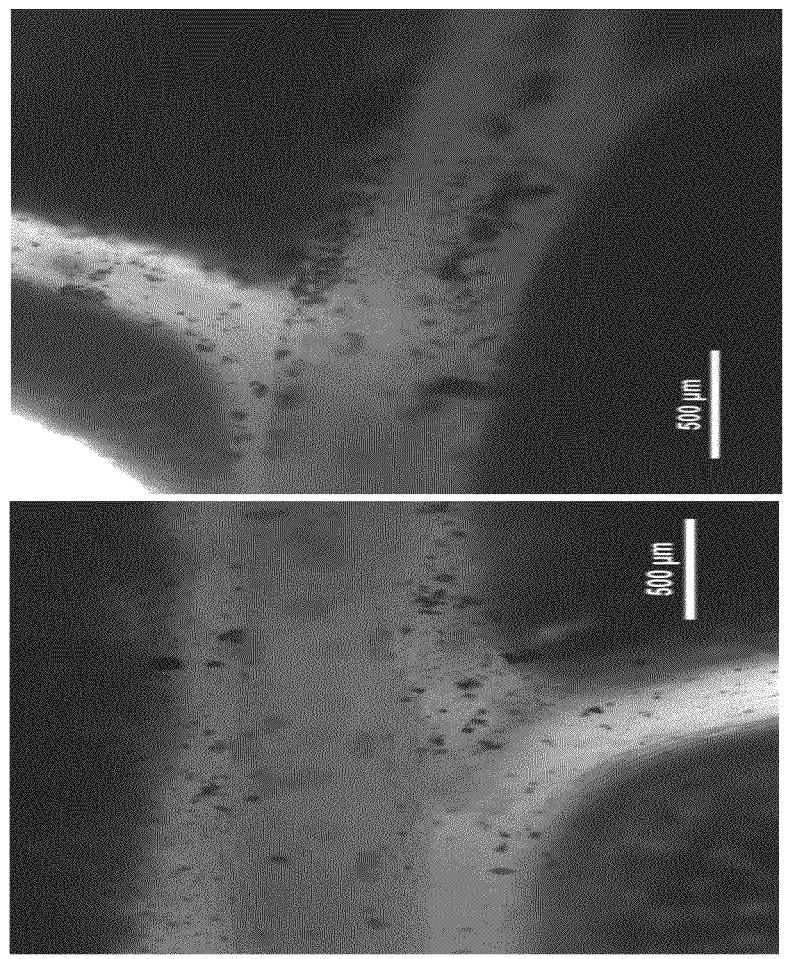

FIGS. 5A-B are images of main and secondary veins of tetraploid (A) and diploid (B) plants.

Figure 6:

FIG. 6 is a photograph showing castor seeds of a Chinese variety (left), Brazilian variety (center), and a tetraploid that was generated by applying the present teachings to the Brazilian variety (right).

DESCRIPTION OF EMBODIMENTS OF THE INVENTION

The present invention, in some embodiments thereof, relates to castor plants and, more particularly, but not exclusively, to polyploid castor plants and methods of generating and using same.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Production of castor (*Ricinus communis* L., Euphorbiaceae) is needed to supply castor oil for the hundreds of products using this versatile chemurgical raw material. Forty to 45 thousand tones of castor oil and derivatives are imported each year (Roetheli et al. 1991) to the U.S.A. to supply the ever increasing needs.

In order to meet these needs, the present inventors have indentified conditions for genome multiplication in castor plant seeds. Genomically multiplied castor seeds generated according to the present teachings provide for progeny plants characterized by as high a yield (e.g., seed yield, oil yield) and fertility as their isogenic diploid castor progenitors. This is in sharp contrast to previous reports of tetraploid castor plants which exhibited low productivity as compared to diploids (see work of Efremov 1972; Evstaf'eva Fedorenko 1972, reported in Moshkin and Doryadinka, 1986).

As is illustrated hereinbelow and in the Examples section which follows, a tetraploid castor plant generated according to the present teachings was qualified for both yield and fertility. Tested parameters included stomatal area, number of stomata per unit area, statistical analysis scaled photographs of the stomata, size of typical leaf veins and chemical analysis of seed oil. The average size of the diploid Castor plant stomata was $150\mu^2 \pm 32$ and that of the tetraploid was $221\mu^2 \pm 96$. The difference was significant at a 0.001 level. Number of stomata was respectively for tetra and diploid 54 and 105 stomata per 1 $mm^2$. Based on these findings and the larger size of the tetraploid plant, it is suggested that the tetraploid plants exhibit higher photosynthetic efficiency per unit area than the diploid plant. The size of the major and the secondary petioles veins was larger for the tetraploid than the diploid plant, in accordance with a polyploid phenotype. The number of seeds per plant was similar in the tetraploid plant as in the isogenic diploid castor plant. Seeds dimension (i.e., length, width and fresh weight) was larger in the tetraploid than in the diploid plants, indicating even higher yield in the tetraploid than the diploid plant. Volumetric oil content was as least as similar to that of the isogenic diploid plant. All these point out to the superiority of the polyploid plants over wild-type castor plants.

Thus, according to an aspect of the present invention there is provided a polyploid castor plant being at least as fertile as a diploid castor plant isogenic to the polyploid castor plant when grown under similar conditions.

As used herein the phrase "castor plant" also termed "castor oil plant" and "*Ricinus communis*", refers to the plant species of the Euphorbiaceae.

The castor plant of some embodiments of the present invention refers to a whole plant or portions thereof, processed or non-processed (e.g., seeds, oil, dry tissue, meal, cake etc.), regenerable tissue culture or cells isolated therefrom.

As used herein the term "polyploid" refers to a plant with three or more sets of chromosomes (e.g., 3N, 4N, 5N, 6N and more). According to some embodiments of this aspect of the present invention, the polyploid plant is an autopolyploid.

As used herein the term "diploid" refers to a typical castor plant having two sets (2N) of chromosomes, whereby each set comprises 20 chromosomes. The diploid castor plant, as used herein is isogenic to the multiplied polyploid plant i.e., both sets of chromosomes contain essentially identical alleles in all locations. The diploid plant may be naturally occurring, genetically modified or a breeding product.

As used herein the term "fertile" refers to the ability to reproduce sexually. Fertility can be assayed using methods which are well known in the art. The following parameters may be assayed in order to determine fertility: the number of seeds; gamete fertility may be determined by pollen germination such as on a sucrose substrate; and alternatively or additionally acetocarmine staining, whereby a fertile pollen is stained.

According to some embodiments of the present invention, a mature polyploid castor plant has at least about the same (+/−10%) number of seeds as it's isogenic diploid progenitor grown under the same conditions; alternatively or additionally the polyploid plant has at least 90% fertile pollen that are stained by acetocarmine; and alternatively or additionally at least 90% of seeds germinate on sucrose.

Comparison assays done for characterizing traits (e.g., fertility, yield, biomass and vigor) of the polyploid plants of the present invention are typically effected in comparison to it's isogenic progenitor (hereinafter, "the diploid plant") when both are being of the same developmental stage and both are grown under similar growth conditions.

Thus, according to some embodiments of the present invention, the polyploid plant has a larger surface area of a leaf than that of the diploid castor plant. In exemplary embodiments leaf area: 30%-100% larger than that of the diploid plant and leaf thickness is at least 1.5-2.5 greater than that of a diploid plant.

According to some embodiments of the present invention, the polyploid plant has a larger stomata surface than that of the diploid castor plant. In an exemplary embodiment the stomata surface area is at least 1.5-2.5 greater than that of the diploid plant.

According to some embodiments of the present invention, the polyploid plant is capable of cross-breeding with a diploid plant.

According to some embodiments of the present invention, the polyploid plant is stable for at least 4, 5, 7, 9 or 10 generations.

According to some embodiments of the present invention, the polyploid plant has seed yield (as determined by at least one of: seed number, seed dimensions and volumetric oil content) at least as similar to the diploid castor grown. According to further embodiments of the present invention, the seed yield exceeds that of the diploid plant by at least about 1, 1.5, 1.75, 2, 2.5, 3 or 5 folds.

As used herein the term "stable" refers to the number of chromosomes and chromosome copies, which remains constant through several generations, while the plant exhibits no substantial decline in at least one of the following parameters: yield, fertility, biomass, vigor Polyploid plants of the present invention can be generated using an improved method of colchicination, as described infra.

Germinating the seeds for 12 hours at a temperature of 25° C. in distilled water. Thereafter soaking the seeds in a multiplication solution comprising: 0.5% colchicine 0.5% DMSO, 0.03% Triton x 100 for 20 hours. Finally, the seeds are washed and seeded in an appropriate germination bed.

Additionally or alternatively, polyploid castor plants of the present invention can be generated using colchicine or any other cell cycle inhibitor (e.g., G2/M phase inhibitors, such as microtubule assembly inhibitors e.g., colchicine, vinblastine, nocodazole, oryzaline and trifluraline), whereby the targeting agent is a magnetic field for targeted delivery of the inhibitor to the chromatin fibers.

A specific embodiment of such a method is provided hereinbelow. Of note, measures are taken to maintain the indicated pH values each phase (such as with HCL or NaOH).

Stage One—3 Hours:

Seeds are incubated in a Petri dish at a temperature of 26° C. in the dark in a vinblastine sulpahte (0.1% v/v) solution comprising 0.5% DMSO titrated to pH 5.6. pH conditions are monitored so as to maintain constant pH (5.6) throughout this phase. The vessel is positioned in a magnetic field of 1300 Gauss, whereby the magnets are located 10.5 cm from each other.

Stage Two—3 Hours:

The seeds are incubated in the above solution in day-light conditions 4° C. and pH is titrated to 6.

Stage Three—6 Hours

The seeds are incubated in day-light conditions 20° C. and pH is titrated to 5.4.

Stage Four—12 Hours

The seeds are incubated in day-light conditions 26° C. and pH is titrated to 6. The magnetic field is removed and Nocodazole is added to a concentration of 5 m/ml.

Stage Five—12 Hours:

The seeds are incubated at day light under constant temperature conditions (26° C.).

The seeds are washed well in water so as to increase pH to 7. Thereafter, the seeds are seeded on appropriate growth beds under long-day light conditions (16 hours) 26° C.

Using these teachings the present inventors were able to generate polyploid castor plants such as that deposited under the Budapest treaty in NCIMB Ltd. and having Accession No. NCIMB 41593 *Ricinus communis* B2-20-4N.

Once established, the castor plants of the present invention can be propagated sexually or asexually such as by using tissue culturing techniques.

As used herein the phrase "tissue culture" refers to plant cells or plant parts from which castor plants can be generated, including plant protoplasts, plant cali, plant clumps, and plant cells that are intact in plants, or part of plants, such as seeds, leaves, stems, pollens, roots, root tips, anthers, ovules, petals, flowers, embryos, fibers and bolls.

According to some embodiments of the present invention, the cultured cells exhibit genomic stability for at least 4, 5, 7, 9 or 10 passages in culture.

Techniques of generating plant tissue culture and regenerating plants from tissue culture are well known in the art. For example, such techniques are set forth by Vasil., 1984. Cell Culture and Somatic Cell Genetics of Plants, Vol I, II, III, Laboratory Procedures and Their Applications, Academic Press, New York; Green et al., 1987. Plant Tissue and Cell Culture, Academic Press, New York; Weissbach and Weissbach. 1989. Methods for Plant Molecular Biology, Academic Press; Gelvin et al., 1990, Plant Molecular Biology Manual, Kluwer Academic Publishers; Evans et al., 1983, Handbook of Plant Cell Culture, MacMillian Publishing Company, New York; and Klee et al., 1987. Ann. Rev. of Plant Phys. 38:467 486.

The tissue culture can be generated from cells or protoplasts of a tissue selected from the group consisting of seeds, leaves, pollens, roots, root tips, anthers, ovules, petals, flowers, embryos, fibers and bolls.

It will be appreciated that the plants of the present invention can also be used in plant breeding along with other castor plants (i.e., self-breeding or cross breeding) in order to generate novel plants or plant lines which exhibit at least some of the characteristics of the castor plants of the present invention.

Plants resultant from crossing any of these with another plant can be utilized in pedigree breeding, transformation and/or backcrossing to generate additional cultivars which exhibit the characteristics of the castor plants of the present invention and any other desired traits. Screening techniques employing molecular or biochemical procedures well known in the art can be used to ensure that the important commercial characteristics sought after are preserved in each breeding generation.

The goal of backcrossing is to alter or substitute a single trait or characteristic in a recurrent parental line. To accomplish this, a single gene of the recurrent parental line is substituted or supplemented with the desired gene from the nonrecurrent line, while retaining essentially all of the rest of the desired genes, and therefore the desired physiological and morphological constitution of the original line. The choice of the particular nonrecurrent parent will depend on the purpose of the backcross. One of the major purposes is to add some commercially desirable, agronomically important trait to the plant. The exact backcrossing protocol will depend on the characteristic or trait being altered or added to determine an appropriate testing protocol. Although backcrossing methods are simplified when the characteristic being transferred is a dominant allele, a recessive allele may also be transferred. In this instance, it may be necessary to introduce a test of the progeny to determine if the desired characteristic has been successfully transferred Likewise, transgenes can be introduced into the plant using any of a variety of established transformation methods well-known to persons skilled in the art, such as: Gressel., 1985. Biotechnologically Conferring Herbicide Resistance in Crops: The Present Realities, In: Molecular Form and Function of the plant Genome, L van Vloten-Doting, (ed.), Plenum Press, New York; Huftner, S. L., et al., 1992, Revising Oversight of Genetically Modified Plants, Bio/Technology; Klee, H., et al., 1989, Plant Gene Vectors and Genetic
Transformation: Plant Transformation Systems Based on the use of *Agrobacterium tumefaciens*, Cell Culture and Somatic Cell Genetics of Plants; and Koncz, C., et al. 1986, Molecular and General Genetics.

It will be appreciated that castor plants of the present invention can be genetically modified such as in order to introduce traits of interest e.g., improved oil composition and enhanced resistance to stress (e.g., biotic or abiotic). Non-limiting examples of nucleic acid sequences useful for altering oil composition of castor plants and methods of castor transformation, as well as nucleic acid constructs useful for same are described in U.S. Pat. No. 6,974,893, which is hereby incorporated by reference in its entirety.

According to some embodiments of the present invention the fatty acid composition of the multiplied castor is about the same as that of the diploid castor plant, although the level of the different components may vary.

Thus, the present invention provides novel castor plants and cultivars, and seeds and tissue culture for generating same.

Castor plants generated based on the present teachings can be further processed to generate castor plant products which are commonly used in for numerous industrial applications, including bio-based lubricants, waxes, paints and coatings, plastics, anti-fungal compounds, and cosmetics.

Thus, according to an aspect of the present invention there is provided a method of producing castor oil, the method comprising: harvesting seeds of the castor plant or plant part as described hereinabove; and processing the seeds so as to produce the castor oil.

Following is a non-limiting description of seed collection and processing.

Castor fruits are harvested when fully mature and the leaves are dry, in about 95-180 days depending on the cultivar. Planting and harvesting may be done by hand methods or be completely mechanized. Harvesting should begin before rainy season in tropical regions, but in dry regions it is best to harvest when all fruits are mature. The spikes are cut or broken off and the capsules stripped off and collected. Unless the capsules are dry, they must be spread out to dry quickly. Sun drying, frost drying or by the use of defoliants. Harvesting machines may be used such as modified wheat headers which shake capsules from plants by jarring plants at their bases. Relative humidity of 45% or less is required for efficient operation with mechanical harvesters. Some indehiscent varieties are threshed by ordinary grain thresher at 400-800 r.p.m. cylinder speed. After harvesting, seeds must be removed from the capsules or hulls, usually with hulling machines if capsules are dry. Percentage of seed to hull averages 65-75, depending upon the maturity of the seed at harvest.

Extraction of oil from castor seeds is done in a manner similar to that for most other oil seeds. The seeds are cleaned, cooked and dried prior to extraction. Cooking is done to coagulate protein (necessary to permit efficient extraction), and to free the oil for efficient pressing.

The first stage of oil extraction is pre-pressing, using a high pressure continuous screw press—called the expeller. Extracted oil is filtered, and the material removed from the oil is fed back into the stream along with fresh material. Material finally discharged from the press, called cake, contains 8 to 10 percent oil. It is crushed into a coarse meal, and subjected to solvent extraction with hexane or heptane.

Once the oil has been extracted from the seed, it is necessary to remove impurities from the oil. The oil is essentially a pure triglyceride, and contains almost 90% of glyceryl tricinoleate. It is the ricinoleic triglyceride that is needed in order to produce high quality castor oil.

The steps to refining the crude oil include:

Settling and Degumming of the oil—Done to remove the aqueous phase from the lipids, and to remove phospholipids from the oil.

Bleaching—Bleaching results in the removal of coloring materials, phospholipids and oxidation products.

Neutralization—The neutralization step is necessary to remove free fatty acids from the oil. This can be done in one of two ways: (a) Alkali (Chemical) or (b) Steam Stripping (Physical) means. Alkali/Chemical Method: Caustic soda (alkali) is mixed in the proper amounts and the aqueous solution is removed, leaving the neutral oil behind. Steam Stripping: This is done under vacuum, to remove moisture, free fatty acids, odor bodies, and other impurities from the oil. As it is performed under vacuum conditions, the oil can be kept at a low temperature, preserving its chemical structure by not subjecting it to temperatures in which undesirable dehydration reactions can occur.

Deodorization of the oil—Deodorization results in the removal of odour from the oil.

Many derivatives can be produced from castor oil. Some of these derivatives have chemical compositions similar to those of petroleum based oils.

Castor Seed Residue, also called Castor Meal—Castor meal is the residue obtained from castor cake by solvent extraction process. It is one of the most versatile natural manures. This manure enhances the fertility of the soil without causing any damage or decay. It is enriched with the three elements vital and conducive to the proper growth of crops i.e., Nitrogen, Phosphorus and Potassium. It also has traces of nutrients like Manganese, Zinc and Copper, thus making it a balanced fertilizer. Moreover, it helps to neutralize the detrimental effects of chemical fertilizers. Apart from their contribution to nutrients, they have a number of benefits in agriculture, which none of the synthetic fertilizers or pesticides can offer. They provide slow and steady nourishment, stimulation, protection from soil nematodes and insects, improve yields, and quality of product like taste, flavor, amino acid composition etc.

The pressed cake obtained after the expression of castor bean. The solvent extracted cake, although rich in protein cannot be used as cattle fodder because of its toxicity. However, it can be used as a fertilizer. The protein content of castor seed meal varies from 21-48% depending upon the extent of decortications. It has an ideal amino acid profile with moderately high Cystine, mithionine, and isoleucine. But its anti nutritional substances, ricin, ricine and an allergen restrict its use in poultry feed, even at a very low level of inclusion.

Hydrogenated Castor Oil (HCO)—also known as castor wax is a hard, brittle, insoluble wax. It is produced by adding hydrogen in the presence of a nickel catalyst. It is mainly used for coatings and greases where resistance to moisture, oils and other petrochemical products is required.

HCO is produced by the hydrogenation of castor oil with nickel catalyst. Its white flakes are extremely insoluble and are water resistant. The main use is in manufacturing greases and in paper coating for food packaging.

Hydrogenated oil is also utilized in the manufacture of waxes, polishes, carbon paper, candles and crayons.

12 Hydroxy Stearic Acid (12 HSA)—12 HSA is an off-white solid fatty acid used to manufacture lithium and calcium based lubricating greases. When reacted with an ester, 12 HSA provides a hard finish for the automotive and small appliance industries.

Methyl 12 HSA (Methyl 12 Hydroxy Stearate Acid, Methyl 12 Hydroxystearate)—Methyl 12HSA is formed by direct esterification of the 12HSA with methanol. It is usually sold in the liquid form and is widely used in the continuous grease process. It has a lower melt point than 12HSA and is, therefore, easier to handle in the liquid form. Greases made with Methyl 12HSA can be formulated to higher drop points, and they experience both less bleeding and improved oxidative stability.

Blown Castor Oil—Blown castor oil is a castor oil derivative that has a higher viscosity and specific gravity than natural castor oil. These properties are induced by bubbling air thorough it at elevated temperatures. Blown castor oil finds use as a plasticizer for inks, lacquers and adhesives.

COLM, Urethane Grade—COLM (castor oil low moisture) is a refined grade of castor oil for specific applications that require minimum moisture. Typical applications include urethane coatings, adhesives and inks. COLM also finds use in urethane blowing and urethane molding.

Dehydrated oil is an excellent drying agent which compares favorably with tung oil and is used in paints and varnishes.

It is expected that during the life of a patent maturing from this application many relevant derivatives will be developed and the scope of the term derivative is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate some embodiments of the invention in a non limiting fashion.

Example 1

Generation of Polyploid Castor Plants

Castor plants from different genetic backgrounds were collected from a number of regions in Israel (Upper Galilee, Lower Galilee, Coastal Plain and the Negev) as well as from different regions of the world (South Brazil, North Brazil, Argentina, Paraguay, North China and Central China). The genomes of these plants were multiplied using Mutation Free Genome Multiplication (MFGM). The multiplication in this experiment was performed using any of the above described protocols.

All sources underwent a process of focused mutagenesis so as to expand the pre-existing genetic variability and locate male sterility in different backgrounds.

The plants that underwent the genome multiplication process were planted in the field and their level of ploidy was checked using a FACS (Fluorescence Activated Cell Sorter).

Briefly, nuclei were released from 2 cm×2 cm leaf tissue by immersion in chopping buffer for 30 seconds.

Chopping buffer consisted of 4.575 gram $MgCl_2$, 2.095 gr.—MOPS, 4.4 gr—Sodium Citrate, 1 gr—DTT, 1.65 gr (10 drops) Triton x 100—all per 500 ml of distilled water. Chopping was done with a razor blade, in one direction. The chopped tissue was transferred to a Petri dish and placed on ice.

The sample was filtered before use (20 mesh). Nuclei samples (2 cc-6 cc) were removed to a FACS tube and 15 µl propidium iodide (PI) was added to each sample. Following 15 min, the samples were analysed in a flow cytometer fitted with a Cyonics argon laser (488 nm) operating at 15 mW.

Fluorescence that exceeded 635 nm is gated and results displayed as single parameter histograms of number of nuclei in each of 1024 channels. Control was fixed to channel 300.

Polyploid plants underwent a pollen fertility test by germination on sucrose bedding and microscopic examination of the pollen grains (as explained above—acetocaramine is used to stain fertile pollen).

Figure 1:

All the plants that were determined to be unharmed both phenotypically and in terms of the look and structure of the pollen grains and which fertility levels was no less than that of the control plants, underwent self pollinations (FIG. 1).

The offspring of the genomically multiplied plants were planted to check stability and gamete fertility. The plants that were selected served as parents in the production of hybrids.

The F2 population underwent genome multiplication using the MFGM technology and the ploidy level of all plants was checked using a FACS.

The plants that tested true for genome multiplication and were also fertile and interesting from the point of view of plant breeding were tested to determine the fertility level of their pollen and were then self-pollinated.

The plants that tested true for genome multiplication and were male-sterile served as parents to hybrids and were pollinated by the said selected genomically multiplied plants.

Example 2

Characterization of Stomata and Seed Markers of Multiplied Castor Oil Plant (Ricinus Communis) Genotypes and their Effects on $CO_2$ Uptake, Transpiration and Yield

Materials and Experimental Procedures

Study region: The study was effected in a typical Mediterranean climate with a long term mean annual temperature of 18-20° C. (minimum and maximum air temperatures were −8-10° C. in January and 30-35° C. in August), 600-700 mm precipitation falls during the winter (November to May)., 1500-2000 mm evapotranspiration and incident PAR of 300-350 MJ $m^{-2}$. Maximum incident PAR occurs in August (410-420 MJ $m^{-2}$ $month^{-1}$) and the minimum in December (1140-160 MJ $m^{-2}$ $month^{-1}$).

The surface soils (0-30 cm) with different proportions of sand, silt, and clay fractions in the study locations were predominantly fine-textured soils displayed a narrow range of variation with respect to field capacity and permanent wilting point which corresponded to −0.03 MPa and −1.5 MPa, respectively, in matric potential. Soil dry bulk densities ranged between 1.22 and 1.35 g $cm^{-3}$. The soils had no salinity problem, and total soluble salt contents were under 0.1%. Soils of the study sites had slightly alkaline pH values of 7.5 to 7.7 and were determined to be poor in soil organic matter (1.18 to 2.37%).

Genetic methods—Castor bean polyploid line treated with the "MFGM" technology was compared with its isogenic diploid line for fertility and yield. For this, single plants from each line were harvested, and number of capsules and yield components were collected per plant.

Photosynthesis and transpiration measurements: Fractions of leaves from the two genotypes were inserted under a microscope Nikon TI inverted microscope equipped with objective 20× super flour and operated with NIS elements software. 30-50 stomata in each treatment were marked, their area was measured automatically and analyzed statistically.

The coupled dynamics of net photosynthetic rate ($P_N$), transpiration rate ($E_T$), water use efficiency (WUE), photosynthetically active radiation (PAR), air temperature (T), relative humidity (RH), and atmospheric $CO_2$ concentration ($C_{atm}$) were measured.

For measuring various environmental and plant parameters the PTM-48M Photosynthesis Monitor was used (FIG. 2A).

The system contains: four self-clamping leaf chambers LC-4A (FIG. 2B) which successively close for two minutes for monitoring $CO_2$ exchange of leaves, infrared $CO_2$ analyzer and a built-in data logger. The monitor also has eleven inputs for additional sensors. The additional sensors used in the current experiment included: PIR-1 Photosynthesis Radiation Sensor ATH-2 Air Temperature and Humidity Sensor, Photosynthesis and transpiration data from four leaf chambers as well as data from the additional sensors were automatically recorded every 30 minutes around-the-clock.

The diploid and the tetraploid plants in the experiment are shown in FIG. 3. The leaf chambers (LC) are given as a reference for the size of the leaves. Note that the leaves of the diploid plant were much smaller than the leaves of the tetraploids.

Fatty acid analysis—oil was trans-esterified by reaction with a solution of Potassium Hydroxide in methanol and tested using Gas Liquid Chromotography (ISO 5509-1978).

Germination assay—seeds were incubated on sucrose beds (2% sucrose and 2 mM $H_3BO_3$) for 12 hours in 26° C. Germination was evaluated thereafter.

Acetocarmine staining—pollen was stained with 1% acetocarmine solution for 15 minutes and then viewed under the microscope.

Statistical Analysis—The stomata analysis was carried out with the NIS software. It included frequency distribution, standard deviation and t-test for significance. The frequency distribution of the stomata was close to normal, t-test results of both number of stomata per unit area and area of stomata was significant at a 0.001 level. The average of two leaf chambers per diploid plant and two chamber were used to measure the multiplied Castor oil plant genotypes. Ambient $CO_2$ was detected with four probes and the standard deviation of the output was calculated. Preliminary test indicated that the coefficient of variation was 0.13 for both photosynthesis and transpiration.

It is expected that the polyploid plants generated according to the present teachings exhibit a similar or even higher photosynthesis than diploid plants, as evidenced by transpiration and photosynthesis assays.

Stomatal area and density—FIG. 4 clearly shows that the size of the tetraploid stomata is larger than that of the diploid, while the number of stomata (density) of the diploid is larger. The statistical data of the two photos are summarized in Table 1, below. The first 4 lines (1-4) summarize the physical properties of the image. Line no. 5 indicates the stomata density which is about 6 time larger for the diploid than the tetraploid.

TABLE 1

The physical properties of the stomata in the leaves of tetra and diploid plants

| | Item | units | Tetraploid | diploid |
|---|---|---|---|---|
| 1 | no. of pixels x Axis | no. | 1,392.0 | 1,392.0 |
| 2 | no. of pixels y Axis | no. | 1,040.0 | 1,040.0 |
| 3 | length of a pixel | μ | 0.3 | 0.3 |
| 4 | Area of a pixel | μ | 0.1 | 0.1 |
| 5 | Average no. of stomata per slide | no. | 8.0 | 47.0 |
| 6 | Average area per stomata | $\mu^2$ | 221.5 | 150.0 |
| 7 | Total area of stomata per slide | $\mu^2$ | 1,772.0 | 7,050.0 |
| 8 | Area of slide | $\mu^2$ | 148,242.4 | 148,242.4 |
| 9 | Area of slide | $mm^2$ | 0.1 | 0.1 |
| 10 | No. of stomata/$mm^2$ | No. | 54.0 | 317.0 |
| 11 | Stomatal area per $mm^2$ | $\mu^2$ | 11,953.4 | 47,557.2 |

Line no. 6 shows that the area of a single tetraploid stomata is about 50% larger than that of the diploid. However, the specific stomatal area (line 11) of the diploid is about 4 times larger than that of the tetraploid (p=0.001).

FIGS. 5A-B are images of the veins of the diploid (B) and tetraploid (A) castor plants. The measured veins of the two plants were taken at the fifth secondary vein above the center of the leaf. The diameter of the major tetraploid vein is about 1500μ while the diameter of the equivalent diploid vein is only half. Similar observation can be found in the secondary veins. It was found 500μ in the tetraploid and less than 300μ in the diploid.

Seed properties—Phenotypic appearance of multiplied castor seeds is shown in FIG. 6. Seeds length, width and fresh weight were significantly larger in the tetraploid than diploid genotypes (Table 2, below). The differences within each group were negligible.

TABLE 2

Comparison[a] of seeds size and fresh weight between a castor diploid (2n) and tetraploid (4n) genotypes.

| Genotype | Obsr. | Length, cm (s.d) | Width, cm (s.d) | Weight, g (s.d) |
|---|---|---|---|---|
| B2-74-1-2 2n | 21 | 1.38 (0.06) bc | 0.83 (0.03) c | 0.34 (0.06) c |
| B2-20(11)-11 4n | 17 | 1.46 (0.05) a | 0.985 (0.03) a | 0.48 (0.04) a |
| B2-20(12)-7 4n | 7 | 1.48 (0.035) a | 1.01 (0.026) a | 0.49 (0.07) a |
| B2(20)98-1 2n | 13 | 1.37 (0.04) bc | 0.85 (0.016) b | 0.36 (0.08) bc |
| B2(20)52-1 2n | 23 | 1.36 (0.04) c | 0.85 (0.03) b | 0.38 (0.035) b |
| B2(20)20 2n | 32 | 1.39 (0.04) b | 0.83 (0.03) c | 0.33 (0.08) c |
| B2(20)29 2n | 44 | 1.39 (0.07) b | 0.85 (0.04) b | 0.34 (0.07) c |
| Mean | | 1.396 | 0.867 | 0.367 |
| F | | 9.7 | 73 | 14.8 |
| Pr > F | | 0.0001 | 0.0001 | 0.0001 |

[a]ANOVA and Tukey range test ($\alpha = 0.05$)

Fertility and yield data: Literature data on polyploid castor bean show a sharp reduction in the polyploid yield and fertility when it was compared with isogenic diploid line or hybrid (Moshkin, V. A. and A. G. Dvoryadinka. Castor Genetics. In Castor. Ed. V.A. Moshkin. Amerind Publ. Co., New Delhi. 1986. pp. 93-102).

Results of data collection of 2N and 4N isogenic lines are presented in Table 3, below.

TABLE 3

Capsule number and seed weight per plant in tetraploid (4n) and diploid (2n) isogenic lines.

| 2N Lines | Capsule number | Total seeds yield (gr) | 4N Lines | Capsule number | Total seeds yield (gr) |
|---|---|---|---|---|---|
| 18-22(43) | 551 | 220 | B2(20)1 | 553 | 287 |
| 18-24(44) | 530 | 213 | B2(20)2 | 542 | 280 |
| 18-28(45) | 542 | 217 | B2(20)3 | 546 | 283 |
| 18-30(46) | 548 | 220 | B2(20)4 | 543 | 280 |
| 18-31(47) | 572 | 229 | B2(20)5 | 570 | 296 |
| 18-35(48) | 546 | 218 | B2(20)6 | 548 | 284 |
| 18-36(49) | 554 | 219 | B2(20)7 | 553 | 287 |
| 18-41(50) | 538 | 214 | B2(20)8 | 540 | 280 |
| 18-42(51) | 541 | 218 | B2(20)9 | 554 | 289 |
| 18-46(52) | 540 | 215 | B2(20)10 | 547 | 284 |
| 18-47(53) | 547 | 218 | B2(20)11 | 555 | 288 |
| 18-49(54) | 543 | 215 | B2(20)12 | 529 | 274 |
| 18-54(55) | 551 | 220 | B2(20)13 | 537 | 279 |
| 18-57(56) | 546 | 218 | B2(20)14 | 541 | 281 |

Thus, it may be concluded that there is no reduction in the fertility of the first generation (and also later generations) polyploid plants compared to the diploid plants.

However, a clear significant difference (by matched pair analysis) in the yield level of the 4N plants compared to the 2N isogenic plants was exhibited. The difference was about 30% increase in the seed yield of the polyploid plants compared to the isogenic diploid plants mainly because of larger seed weight of the polyploids.

Seeds fatty acid profile: The main castor seed fatty acids are oleic, ricinoleic and linoleic (Table 4, below). The present results show that the difference in acid content between tetraploid and diploid lines is not greater than between plants in each line. This strongly indicates that duplication of source plants caused no severe mutations that may interfere in plant basic functions.

TABLE 4

Fatty acid profile of castor diploid (2n) and tetraploid (4n) lines.

| | Line code | | | | |
|---|---|---|---|---|---|
| | B2 (807) | B2(11)20 | I3(4)B | I3(3) 35 | EXPR 20 |
| ploidy level | 2N | 4N | 2N | 4N | 4N |
| Generation | F5 | F5 | F5 | F5 | F1 |
| C 8:0 | — | 0.01 | — | 0.01 | — |
| C10:0 | — | — | — | 0.01 | — |

TABLE 4-continued

Fatty acid profile of castor diploid (2n) and tetraploid (4n) lines.

| | Line code | | | | |
|---|---|---|---|---|---|
| | B2 (807) | B2(11)20 | I3(4)B | I3(3) 35 | EXPR 20 |
| C 12:0 | — | — | — | — | — |
| C 14:0 | — | 0.01 | 0.01 | 0.02 | — |
| C 14:1 | — | — | — | — | — |
| C 15:0 | 0.02 | 0.02 | 0.01 | 0.01 | — |
| C 16:0 | 1.46 | 1.68 | 1.52 | 1.70 | 1.85 |
| C 16:1 | 0.01 | 0.02 | 0.01 | 0.02 | 0.02 |
| C 17:0 | 0.03 | 0.06 | 0.06 | 0.06 | 0.03 |
| C 17:1 | 0.02 | 0.15 | 0.13 | 0.15 | 0.02 |
| C 18:0 | 1.09 | 1.19 | 1.68 | 1.46 | 1.44 |
| C 18:1 (Oleic acid) | 4.78 | 4.39 | 4.91 | 5.90 | 5.63 |
| C 18:1 OH (Ricinoleic acid) | 83.56 | 83.94 | 83.75 | 83.37 | 82.90 |
| C 18:2 (Linoleic acid) | 7.02 | 6.68 | 5.93 | 5.58 | 6.54 |
| C 18:3 | 0.68 | 0.64 | 0.59 | 0.56 | 0.60 |
| C 19:1 | 0.02 | 0.01 | 0.02 | 0.01 | 0.02 |
| C 20:0 | 0.05 | 0.04 | 0.07 | 0.07 | 0.06 |
| C 20:1 | 0.56 | 0.46 | 0.47 | 0.46 | 0.48 |
| C 20:2 | 0.10 | 0.10 | 0.10 | 0.09 | 0.10 |
| C 20:3 | 0.02 | — | — | — | — |
| C 20:4 | 0.02 | — | 0.07 | — | 0.02 |
| C 20:5 n3 | — | — | — | — | — |
| C 21:0 | — | — | — | — | — |
| C 22:0 | 0.03 | 0.01 | 0.01 | 0.01 | — |
| C 22:1 | — | — | 0.02 | — | 0.01 |
| C 22:2 | 0.10 | 0.09 | 0.06 | 0.04 | 0.08 |
| C 22:3 | — | — | 0.02 | — | — |
| C 22:5 n3 | — | — | — | — | — |
| C 22:6 n3 | — | — | — | — | — |
| C23:0 | — | — | — | — | — |
| C 24:0 | 0.02 | 0.02 | 0.02 | 0.02 | 0.02 |
| C 24:1 | — | — | — | — | — |
| Sum | 99.59 | 99.51 | 99.46 | 99.53 | 99.82 |

Volumetric Oil content—Table 5 below demonstrates the oil content in 3N plants. The results indicate that the 3N plants have similar oil content to the 2N plants.

TABLE 5

| 1 | Par - 21 | 42.40 | Control | 2N |
|---|---|---|---|---|
| 2 | B1 - 19 | 41.00 | Control | 2N |
| 3 | CH - 2 | 41.70 | Control | 2N |
| 4 | C - 181 | 44.10 | Control | 2N |
| 6 | EXPR 10 | 47.40 | | 2N |
| 7 | EXPR 11 | | | 2N |
| 8 | EXPR 12 | | | 2N |
| 9 | EXPR 13 | 47.10 | | 2N |
| 10 | EXPR 14 | 42.80 | | 2N |
| 11 | EXPR 15 | 41.80 | | 2N |
| 12 | EXPR 16 | | | 2N |
| 13 | EXPR 17 | | | 2N |
| 14 | EXPR 18 | 43.10 | | 2N |
| 15 | EXPR 19 | 44.50 | | 2N |
| 16 | EXPR 26 | 46.00 | | 3N |
| 17 | EXPR 27 | 44.10 | | 3N |
| 18 | EXPR 29 | 42.70 | | 3N |
| 19 | EXPR 31 | | | 3N |
| 20 | EXPR 33 | | | 3N |
| 21 | EXPR 39 | | | 2N |
| 22 | EXPR 40 | 44.70 | | 2N |
| 23 | EXPR 44 | 48.10 | | 2N |
| 24 | EXPR 46 | 47.60 | | 2N |
| 25 | EXPR 50 | 43.80 | | 3N |
| 26 | EXPR 55 | 44.70 | | 2N |
| 27 | EXPR 60 | | | 3N |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Other References are Cited Throughout the Application

1. Dhawan, O. P. (1996) Enhancing the productivity of secondary metabolites via induced polyploidy: a review. *Euphytica* 87(2)
2. Moshkin, V. A. and A. G. Dvoryadinka. Castor Genetics. In Castor. Ed. V. A. Moshkin. Amerind Publ. Co., New Delhi. 1986. pp. 93-102.
3. Nagl, W. (1984) The fluorophenylalanine sensitive and resistant tobacco cell lines, TX1 and TX 4 1. DNA contents, chromosome numbers, nuclear ultrastructures, and effects of spermidine. *PROTOPLASMA* 122
4. Darren J. Obbard, Stephen A. Harris, Richard J. A. Buggs, John R. Pannell (2006) HYBRIDIZATION, POLYPLOIDY, AND THE EVOLUTION OF SEXUAL SYSTEMS IN MERCURIALIS (EUPHORBIACEAE) Evolution 60 (9), 1801-1815. doi:10.1111/j.0014-3820.2006.tb00524.x
5. M. P. Timko, A. C. Vasconcelos (1981) Ptiotosynthetic activity and chloroplast membrane polypeptides in euploid cells of *Ricinus* Physiologia Plantarum 52 (2), 191-196.
6. Comparative study of chlorophyll content in diploid and tetraploid black wattle Mathura et al. *Forestry*. 2006; 79: 381-388

What is claimed is:

1. A castor plant as deposited under the Budapest treaty in NCIMB Ltd. and having Accession No. NCIMB 41593 Ricinus communis B2-20-4N.

2. A plant part comprising plant cells of the castor plant of claim 1.

3. The plant part of claim 2 being a seed.

4. An isolated regenerable cell of the castor plant of claim 1.

5. The cell of claim 4, exhibiting genomic stability for at least 5 passages in culture.

6. The cell of claim 4 being from a meristem, pollen, a leaf, a root, a root tip, an anther, a pistil, a flower, a seed or a stem.

7. A tissue culture comprising the regenerable cell of claim 4.

8. A method of producing castor seeds, comprising self-breeding or cross-breeding the plant of claim 1 with a tetraploid castor plant.

9. A method of producing castor oil, the method comprising:
   (a) harvesting seeds of the castor plant of claim 1; and
   (b) processing said seeds so as to produce the castor oil.

* * * * *